United States Patent [19]

Cherkofsky et al.

[11] 4,182,769
[45] Jan. 8, 1980

[54] ANTI-INFLAMMATORY 1-SUBSTITUTED-4,5-DIARYL-2-(SUBSTITUTED-THIO) IMIDAZOLES AND THEIR CORRESPONDING SULFOXIDES AND SULFONES

[75] Inventors: Saul C. Cherkofsky, Wilmington, Del.; Thomas R. Sharpe, Fort Salonga, N.Y.

[73] Assignee: E. I. Du Pont de Nemours and Company, Wilmington, Del.

[21] Appl. No.: 865,831

[22] Filed: Jan. 5, 1978

Related U.S. Application Data

[63] Continuation-in-part of Ser. No. 767,219, Feb. 9, 1977, abandoned.

[51] Int. Cl.² .................. C07D 233/84; C07D 405/04; A61K 31/415
[52] U.S. Cl. .................. 424/273 R; 548/336; 548/337
[58] Field of Search .................. 548/336, 337; 424/273 R

[56] References Cited

U.S. PATENT DOCUMENTS

| | | | |
|---|---|---|---|
| 3,629,473 | 12/1971 | Doebel et al. | 260/294.8 G |
| 3,707,475 | 12/1972 | Lombardino | 260/294.8 R |
| 3,850,944 | 11/1974 | Tanaka et al. | 260/294.8 G |
| 3,929,807 | 12/1975 | Fitzi | 260/294.8 G |

OTHER PUBLICATIONS

Bhatt et al., I Chem. Abst. 1948, vol. 42, col. 8799.
Bhatt et al., II Chem. Abst. 1954, vol. 48, col. 3967.
Kochergin et al., Chem. Abst. 1956, vol. 50, cols. 9387–9388.
Lempert et al., Chem. Abst. 1965, vol. 63, col. 13238.
Zaur et al., Chem. Ber. 1973, vol. 106, pp. 1628–1636.

Primary Examiner—Natalie Trousof

[57] ABSTRACT

Anti-inflammatory 1-substituted-4,5-diaryl-2-(substituted-thio) imidazoles and their corresponding sulfoxides and sulfones useful for treating arthritis and related diseases.

50 Claims, No Drawings

ANTI-INFLAMMATORY 1-SUBSTITUTED-4,5-DIARYL-2-(SUBSTITUTED-THIO) IMIDAZOLES AND THEIR CORRESPONDING SULFOXIDES AND SULFONES

CROSS REFERENCE TO RELATED APPLICATIONS

This application is a continuation-in-part of prior Application Ser. No. 767,219, filed Feb. 9, 1977 now abandoned.

BACKGROUND OF THE INVENTION

This invention relates to anti-inflammatory imidazoles.

Lombardino, in U.S. Pat. No. 3,707,475 discloses anti-inflammatory 4,5-diaryl-2-substituted imidazoles.

Doebel, in U.S. Pat. Nos. 3,505,350 and 3,651,080, respectively, discloses anti-inflammatory 4-alkyl-5-aryl-1-substituted-2-mercapto imidazoles and 4-alkyl-2-alkylthio-5-aryl-1-substituted imidazoles.

Zauer, K., et al., in Chem. Ber. 106, 1638 (1973), disclose 4,5-bis(4-methoxyphenyl)-2-methylthioimidazole and 4,5-bis(4-chlorophenyl)-2-methylthioimidazole but do not suggest any use.

A number of references, such as Current Sci. India 17, 184-85 (1948) and Acta. Chem. Acad. Sci. Hung. 79 (2) 197-212 (1973) disclose 2-(substituted-thio)-4,5-diphenylimidazoles and 1-methyl-2-(substituted-thio)-4,5-diphenylimidazoles with substituents such as methyl, propyl, allyl, and acetonyl.

There is a continuing need for safe and effective anti-inflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and anti-inflammatory drugs are often used in their treatment. The usefulness of most commercial anti-inflammatories is limited because of toxicity and adverse side-effects. Many produce gastric irritation and other effects, such as changes in blood cells and central nervous system. Adreno-cortical steroids produce gastric irritation and suppression of normal adrenal function.

The present invention results from efforts to develop new anti-arthritic compounds with good anti-inflammatory activity and minimal side effects that could be more effective in treating arthritis than presently available drugs.

In addition to anti-inflammatory activity, some of the compounds of this invention have demonstrated analgesic activity in a test procedure. This additional property is desirable in treatment of arthritis or related diseases; however, such compounds can be employed solely to alleviate pain.

In addition, some of the compounds of this invention are useful as intermediates to compounds which also have anti-inflammatory and/or analgesic activity (see our application Ser. No. 779,805 filed Mar. 18, 1977).

SUMMARY

According to this invention there is provided compounds of formula I and processes for their manufacture, pharmaceutical compositions containing them, and methods of using them to treat arthritis or alleviate pain in mammals.

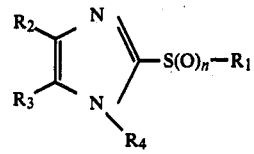

where
$n=0$, 1, or 2;
$R_1 = C_1-C_6$ alkyl; allyl; vinyl; $-CH_2COCH_3$; $-CH_2S(O)_m CH_3$, where $m=0$, 1, or 2; mono- and polyhalo- $C_1-C_4$ alkyl;
$R_2$ and $R_3$, the same or different =

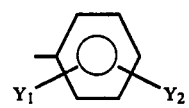

$Y_1$ and $Y_2$, the same or different = hydrogen, $C_1-C_4$ alkoxy, $C_1-C_4$ alkyl, Cl, F, $CF_3$, $NH_2$, $-N(CH_3)_2$, $NO_2$, $CH_3S-$, $CH_3SO_2$, or $Y_1$ and $Y_2$ taken together forming a dioxymethylene bridge;
provided, when $R_1 = C_1-C_4$ alkyl, $C_3-C_4$ haloalkyl with halogen substituted at the 3 or 4 position, allyl, or acetonyl both $Y_1$ and $Y_2$ cannot be H;
$R_4 = C_1-C_6$ alkyl, allyl,

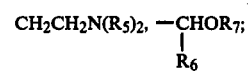

2-tetrahydropyranyl,
2-tetrahydrofuranyl,

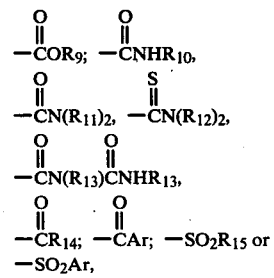

where
$R_5$ = methyl or ethyl;
$R_6$ = H or methyl;
$R_7 = C_1-C_3$ alkyl, benzyl, $-CH_2CH_2OCH_3$

$R_8 = C_1-C_4$ alkyl or benzyl;
$R_9 = C_1-C_4$ alkyl or benzyl;
$R_{10} = C_1-C_6$ alkyl;
$R_{11}$ = H, methyl or ethyl;
$R_{12}$ = H, methyl or ethyl;
$R_{13} = C_1-C_6$ alkyl;
$R_{14} = C_1-C_6$ alkyl;
$R_{15} = C_1-C_4$ alkyl;

Ar=

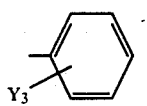

where
$Y_3$=H, F, Cl, Br, $C_1$-$C_4$ alkyl $C_1$-$C_4$ alkoxy or nitro;
provided when

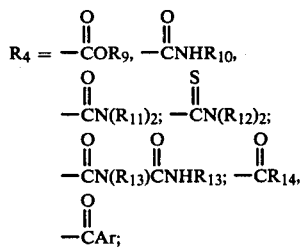

—$SO_2R_{15}$ or —$SO_2Ar$, then n must be 0.

DETAILED DESCRIPTION

Preferred Compounds

Compounds preferred for their antiarthritic activity are those where $R_1$=—$CF_2CF_2H$.
Also preferred are those compounds where $R_1$=$CF_3$.
Also preferred are those compounds where
$R_2$ and $R_3$, independently, =

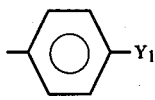

where $Y_1$=H, Cl, or F;
Also preferred are those compounds where
$R_4$=alkoxycarbonyl, alkoxymethyl, benzyloxymethyl, or pivaloyloxymethyl.
Also preferred are those compounds where
n=0, 1 or 2.
More preferred are those compounds where:
$R_1$=—$CF_2CF_2H$;
$R_2$ and $R_3$, independently, =

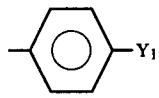

where $Y_1$=H, Cl, or F; and
$R_4$=alkoxycarbonyl, alkoxymethyl, benzyloxymethyl, or pivaloyloxymethyl,
Also more preferred are those compounds where
$R_1$=$CF_3$;
$R_2$ and $R_3$, independently, =

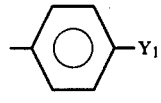

where $Y_1$=H, Cl, or F; and $R_4$=alkoxycarbonyl, alkoxymethyl, benzyloxymethyl, or pivaloyloxymethyl.
Specifically preferred are the following compounds:
1-benzyloxymethyl-4,5-diphenyl-2-(1,1,2,2-tetrafluoroethylthio)imidazole.
4,5-diphenyl-1-ethoxycarbonyl-2-(1,1,2,2-tetrafluoroethylthio)imidazole.
1-benzyloxymethyl-4,5-diphenyl-2-(1,1,2,2-tetrafluoroethylsulfonyl)imidazole.
4,5-diphenyl-1-(2-tetrahydropyranyl)-2-trifluoromethylthioimidazole.
1-ethoxycarbonyl-4,5-bis(4-fluorophenyl)-2-(1,1,2,2-tetrafluoroethylthio)imidazole.
1-ethoxycarbonyl-4(or 5)-(4-fluorophenyl)-5(or 4)-phenyl-2-(1,1,2,2-tetrafluoroethylthio)imidazole.
4,5-bis(4-fluorophenyl)-1-(pivaloyloxymethyl)-2-(1,1,2,2-tetrafluoroethylsulfonyl)imidazole.

Compounds preferred for their analgesic activity are those where at least one of $R_2$ and $R_3$=

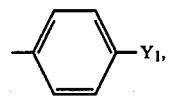

where $Y_1$=$C_1$-$C_4$ alkoxy.

Compounds preferred as intermediates to other antiinflammatory and/or analgesic compounds with $R_4$=H are those where $R_4$=—$CH_2OCH_2C_6H_5$, 2-tetrahydropyranyl, 2-tetrahydrofuranyl, or —$SO_2Ar$.

Synthesis

Compounds unsubstituted in the 1-position ($R_4$ in formula I would be H) are disclosed and claimed in applicants' copending application Ser. No. 779,805 filed Mar. 18, 1977 which is a continuation in part of Ser. No. 691,682 filed June 9, 1976, now abandoned. They can be prepared as follows: benzoin or an approximately substituted benzoin prepared as described in Ide, W. S. and Buck, J. S., *Organic Reactions*, Vol. IV, p. 629, is condensed with thiourea in refluxing dimethylformamide or other high boiling, polar solvents to give a 4,5-diaryl-2-mercaptoimidazole. A similar condensation procedure is described in Kochergin, P. M., *Zhur. Obshchei Khim.*, 31, 1093 (1961); *Chem. Abstr.* 55, 23503f.

Alternatively, reaction of benzoin or substituted benzoins with ammonium thiocyanate at lower temperatures in polar solvents, such as ethanol or 1-propanol, can be used to prepare 4,5-diaryl-2-mercaptoimidazoles.

4,5-Diaryl-2-mercaptoimidazoles can also be prepared by heating 4,5-diarylimidazoles with sulfur at temperatures in the range of 150°–300° either with or without solvent. One suitable solvent for this reaction is tetramethylene sulfone. This procedure is analogous to the conversion of 1-methylbenzimidazole to 2-mercapto-1-methylbenzimidazole as described in A. V. El'tsov and K. M. Krivozheiko, Zh. ob. Kh., 2, 189 (1966).

The appropriate $R_1$ group can be introduced by alkylating the 4,5-diaryl-2-mercaptoimidazole with a suitable alkylating agent such as ethyl iodide or 2,2,2-trifluoroethyl trichloromethanesulfonate. These procedures and the use of other alkylating agents can be found in the Examples.

Also, the 4,5-diaryl-2-mercaptoimidazole can be reacted with tetrafluoroethylene to provide 4,5-diaryl-2-(1,1,2,2-tetrafluoroethylthio)imidazole derivatives. Similar addition reactions of tetrafluoroethylene and other fluorinated olefins are described in England, D. C., et al., *J. Am. Chem. Soc.* 82, 5116 (1960) and Rapp, K. E., et al., *J. Am. Chem. Soc.* 72, 3642 (1950). In certain instances the polyhaloalkyl moiety can then be further modified chemically. For example, imidazoles containing the 2-(2-bromo-1,1,2-trifluoroethylthio) substituent can be converted to 2-(1,1,2-trifluoroethylthio)imidazoles by reduction with tri-n-butyltin hydride or other suitable reducing agents. For the purpose of this disclosure tetrafluoroethylene and other fluorinated olefins used are considered alkylating agents.

The 4,5-diaryl-2-(substituted-thio) imidazole can then be oxidized to the corresponding sulfoxide or sulfone by using oxidizing agents such as m-chloroperbenzoic acid, Tweit, R. C., et al., *J. Med. Chem.* 16, 1161 (1973), sodium metaperiodate, Leonard, N. J. and Johnson, C. R., *J. Org. Chem.* 27, 282 (1962), hydrogen peroxide, Kochergin, P. M. and Shchukina, M. N., *J. Gen. Chem. U.S.S.R.* 25, 2289 (1955), or potassium permanganate, Rapp, K. E. et al. loc. cit.

The appropriate $R_4$ substituent can often be introduced by direct alkylation, acylation, or sulfonylation of the compounds of formula I where $R_4 = H$. This reaction can be carried out in the absence or presence of a base, such as potassium carbonate, pyridine, triethylamine, potassium t-butoxide, methyl lithium or the like. The reaction can be run neat, using the reagent as solvent, or in the presence of an inert solvent, including but not limited to dimethylformamide, glyme, THF, pyridine, methylene chloride. The temperature of the reaction can be in the range $-78°$ C. to the boiling point of the solvent or reagent, if used in excess as the solvent. Examples of alkylating, acylating and sulfonylating agents that can be employed are alkyl halides such as methyl iodide; dimethylaminoethyl chloride; alkoxymethyl halides, such as benzyloxymethyl chloride; acyloxymethyl halides, such as chloromethylpivalate; dihydropyran; 2-chlorotetrahydrofuran; alkyl chloroformates, such as ethyl chloroformate; alkyl isocyanates, such as methylisocyanate; dialkylcarbamoyl chlorides, such as diethylcarbamoyl chloride; dialkylthiocarbamoyl chlorides, such as diethylthiocarbamoyl chloride; alkanoic anhydrides and alkanoyl halides, such as acetic anhydride; aroyl halides, such as benzoyl chloride; alkanesulfonyl halides such as methanesulfonyl chloride; arylsulfonyl halides such as benzenesulfonyl chloride.

Alternatively, the $R_4$-substituent can be introduced by first reacting a 4,5-diarylimidazole with an appropriate reagent such as methyl iodide, allyl bromide, 2-dimethylaminoethyl chloride, benzyl chloromethyl ether, dihydropyran, 2-chlorotetrahydrofuran or benzenesulfonyl chloride. The resulting 4,5-diaryl-1-(substituted)imidazole is then treated with a strong base, such as n-butyl lithium, followed by a fluorinated alkyl-sulfenyl halide, disulfide, or sulfonic anhydride. Typical of these reagents are $CF_3SCl$, $CF_3SSCF_3$, and $(CF_3SO_2)_2O$. Compounds of formula I in which $R_1 = CF_3$ are conveniently prepared by this method.

Compounds of formula I in which $R_4$=alkyl can also be prepared as follows: benzoin or an appropriately substituted benzoin is condensed with an N-alkylthiourea in refluxing dimethylformamide or other high boiling, polar solvent to give a 1-alkyl-4,5-diaryl-2-mercaptoimidazole. The appropriate $R_1$ group can then be introduced as described above.

The preparation of these compounds is further illustrated by the following Examples. Parts are by weight unless otherwise specified, and all temperatures are in degrees centigrade.

EXAMPLE 1

1-Benzyloxymethyl-4,5-diphenyl-2-trifluoromethylthioimidazole

A mixture of 8.8 g (0.04 mole) 4,5-diphenylimidazole, 7.8 g (0.05 mole) benzyl chloromethyl ether, 13.8 g (0.1 mole) potassium carbonate in 100 ml DMF was stirred at RT. After six hours, TLC indicated a single product spot and some remaining starting material. Another 7.8 g (0.05 mole) benzyl chloromethyl ether was added and the mixture was stirred overnight. At this time, TLC showed only a trace of starting material. The mixture was poured into 500 ml water and extracted three times with ether. The ether extracts were backwashed three times with water, then dried and concentrated. The residue was chromatographed on 2 lb. SilicAR CC-7, eluting with mixtures of toluene and ethyl acetate. Eluted with 80/20 toluene/ethyl acetate was 3.1 g (22.8%) of the expected 1-benzyloxymethyl-4,5-diphenylimidazole (recrystallized from hexane), m.p. 97.5°–98.5°.

Anal. Calcd for $C_{23}H_{20}N_2O$: C, 81.15; H, 5.92; N, 8.23. Found: C, 81.33; H, 5.95; N, 8.43.

In glassware dried with a heat gun and under nitrogen, to a mixture of 1.7 g (5 mmole) of 1-benzyloxymethyl-4,5-diphenylimidazole in 25 ml THF and 25 ml ether at $-78°$ was added dropwise a solution of 3.75 ml of 1.6 M n-butyl lithium solution in hexane in 25 ml ether. The reaction mixture was stirred at $-78°$ ca. 15 minutes then 0.8 g (6 mmole) of trifluoromethanesulfenyl chloride (TOXIC) was added as a gas. The mixture was stirred at $-78°$ for 2 hours, then RT overnight. The mixture was added to 200 ml water and neutralized with sodium bicarbonate. The mixture was extracted with ether and the ether extracts were dried and concentrated. The residue was chromatographed on 200 g SilicAR CC-7, eluting with toluene to give, after recrystallization from hexane, 0.5 g (23%) of product, mp 97°–8°.

Anal. Calcd $C_{24}H_{19}F_3N_2OS$: C, 65.44; H, 4.35; N, 6.36. Found: C, 65.62; H, 4.53; N, 6.38.

EXAMPLE 2

1-Benzyloxymethyl-4,5-diphenyl-2-(1,1,2,2-tetrafluoroethylthio)imidazole

A mixture of 3.5 g (0.01 mole) of 4,5-diphenyl-2-(1,1,2,2-tetrafluoroethylthio)imidazole, 2.1 g (0.013 mole) benzyl chloromethyl ether, 3.6 g (0.026 mole) potassium carbonate in 25 ml DMF was stirred for 24 hours. TLC showed some starting material, so an additional 0.5 g (0.003 mole) of benzyl chloromethyl ether was added and stirring continued for another 24 hours. The mixture was poured into ice water, extracted three times with ether and the ether layers backwashed three times with water. The ether solution was dried and concentrated on a rotary evaporator. The residue was chromatographed on 200 g SilicAR CC-7, eluting with toluene to give, after recrystallization from hexane, 3.6 g (76.6%) of white product, mp 70°–70.5°.

Anal. Calcd for $C_{25}H_{20}F_4N_2OS$: C, 63.55; H, 4.27; N, 5.93. Found: C, 63.19; H, 4.27; N, 6.10.

EXAMPLE 3

4,5-Diphenyl-1-ethoxycarbonyl-2-(1,1,2,2-tetrafluoroethylthio)imidazole

A mixture of 1.76 g (5 mmole) 4,5-diphenyl-2-(1,1,2,2-tetrafluoroethylthio)imidazole, 1.1 g (10 mmole) of ethyl chloroformate in 10 ml pyridine was stirred at RT overnight. TLC showed some starting material, so another 0.6 g (5 mmole) of ethyl chloroformate was added and stirring was continued another 24 hours. The mixture was poured into water, neutralized with acetic acid and extracted three times with ether. The ether extracts were backwashed three times with water, then dried and concentrated. The last traces of pyridine were removed by pumping at 50° (0.5 mm). The residue was chromatographed on 150 g SilicAR CC-7, eluting with toluene to give, after recrystallization from hexane, 1.05 g (55%) of white product, mp 126.5°-127°.

Anal. Calcd for $C_{20}H_{16}F_4N_2O_2S$: C, 56.60; H, 3.80; N, 6.60. Found: C, 56.76, 56.78; H, 3.95, 3.88; N, 6.69, 7.01.

EXAMPLE 4

1-Benzyloxymethyl-4,5-diphenyl-2-(1,1,2,2-tetrafluoroethylsulfonyl)imidazole A mixture of 1.92 g (5 mmole) of 4,5-diphenyl-2-(1,1,2,2-tetrafluoroethylsulfonyl)imidazole, 1.6 g (10 mmole) of benzyl chloromethyl ether, 2.8 g (20 mmole) of potassium carbonate in 20 ml DMF was stirred at RT for six hours, then poured into ice water. The aqueous mixture was extracted three times with ether. The ether extracts were backwashed three times with water, then dried and concentrated. The residue was chromatographed on 150 g SilicAR CC-7, eluting with toluene to give, after recrystallization from hexane, 2.5 g (100%) of white product, mp 97.5°-98.5°.

Anal. Calcd for $C_{23}H_{20}F_4N_2O_3S$: S, 59.52; H, 4.00; N, 5.55. Found: C, 59.73; H, 3.70; N, 5.58.

EXAMPLE 5

4,5-Diphenyl-1-(2-tetrahydropyranyl)-2-trifluoromethylthioimidazole

A mixture of 27 g (0.122 mole) 4,5-diphenylimidazole, 21 g (0.25 mole) dihydropyran, 250 ml ethyl acetate and 4.0 g $BF_3.Et_2O$ was refluxed for five days. The nearly clear solution was diluted with ether and filtered to remove 0.6 g insoluble starting material. The ether filtrate was washed several times with 10% $NaHCO_3$ then dried and evaporated. TLC showed starting material still present, so the crude product was chromatographed on 2 lb. SilicAR CC-7, eluting with toluene containing 20 to 40% ethyl acetate. The pure 4,5-diphenyl-1-(2-tetrahydropyranyl) imidazole thus obtained weighed 30.3 g (82%) and had mp 170°-171°.

Anal. Calcd for $C_{20}H_{20}N_2O$: C, 78.92; H, 6.62; N, 9.20. Found: C, 78.57; H, 6.89; N, 9.07.

In glassware dried with a heat gun and under nitrogen, to a mixture of 1.5 g (5 mmole) of 4,5-diphenyl-1-(2-tetrahydropyranyl)imidazole in 20 ml THF and 20 ml ether at −78° was added dropwise a solution of 3.75 ml (6 mmole) of 1.6 M n-butyl lithium in hexane in 20 ml ether. To the light yellow solution was added dropwise after 15 minutes at −78° a solution of 1.2 g (6 mmole) trifluoromethyldisulfide (TOXIC) in 10 ml ether. The dark solution was stirred at −78° for 1 hour, then RT one-half hour (overnight is not detrimental). The mixture was added to water and extracted three times with ether (pH of aqueous layer ∼6). The ether extracts were dried and concentrated. The residue was chromatographed on 150 g SilicAR CC-7, eluting with toluene to give, after recrystallization from hexane, 0.55 g of product, mp 104°-5°.

Anal. Calcd for $C_{21}H_{19}F_3N_2OS$: C, 62.36; H, 4.74; N, 6.93. Found: C, 62.70; H, 4.83; N, 6.91.

EXAMPLE 6

1-Ethoxycarbonyl-4,5-bis(4-fluorophenyl)-2-(1,1,2,2-tetrafluoroethylthio)imidazole To an ice-cooled mixture of 4,5-bis(4-fluorophenyl)-2-(1,1,2,2-tetrafluoroethylthio)imidazole (1.5 g) in pyridine (20 ml) was added ethyl chloroformate (1.3 g). The progress of the reaction was monitored by thin layer chromatography. Additional ethyl chloroformate (7.0 g, added in three portions) and warming to room temperature were required to force the reaction to completion. The reaction mixture was poured into water, and the crystalline solid was collected and washed with water. There was obtained 1.2 g of colorless product, mp 137°-139°.

Anal. Calcd for $C_{20}H_{14}F_6N_2O_2S$: C, 52.17; H, 3.07; N, 6.09. Found: C, 52.08; H, 3.24; N, 5.95.

EXAMPLE 7

Mixture of 1-Ethoxycarbonyl-4-(4-fluorophenyl)-5-phenyl-2-(1,1,2,2-tetrafluoroethylthio)imidazole and 1-Ethoxycarbonyl-5-(4-fluorophenyl)-4-phenyl-2-(1,1,2,2-tetrafluoroethylthio)imidazole To a mixture of 4 (or 5)-(4-fluorophenyl)-5(or 4)-phenyl-2-(1,1,2,2-tetrafluoroethylthio)imidazole (5.0 g, 0.014 mole), pyridine (2.2 g, 0.028 mole), and methylene chloride (75 ml) was added dropwise ethyl chloroformate (3.0 g, 0.028 mole). The mixture was allowed to reflux for 30 minutes. Additional ethyl chloroformate (5 g, added in three portions) was added. After each portion of ethyl chloroformate was added, the mixture was allowed to reflux for 30 minutes. The cooled mixture was washed twice with water, dried ($MgSO_4$), and concentrated. The residue was recrystallized from methylcyclohexane to give 4.3 g (72%) of colorless crystals, mp 132°-135°. NMR indicated this product to be a mixture of the title compounds.

Anal. Calcd for $C_{20}H_{15}F_5N_2O_2S$: C, 54.30; H, 3.42; N, 6.33. Found: C, 54.67; H, 3.70; N, 6.32.

EXAMPLE 8

4,5-bis(4-Fluorophenyl)-1-methyl-2-(1,1,2,2-tetrafluoroethylsulfonyl)imidazole A mixture of 4,5-bis(4-fluorophenyl)-2-(1,1,2,2-tetrafluoroethylsulfonyl)imidazole (3.0 g, 0.0071 mole), methyl iodide (1.5 g, 0.011 mole), potassium carbonate (1.5 g, 0.011 mole), and dimethylformamide (30 ml) was stirred for 50 hours at room temperature in a stoppered flask. The mixture was then poured into water, and after the oil crystallized, the solid was collected and washed with water. There was obtained 2.9 g of colorless crystals, mp 122°-124°. Recrystallization from heptane (125 ml) gave 2.5 g (81%) of colorless prisms, mp 125°-126.5°.

Anal. Calcd for $C_{18}H_{12}N_2F_6O_2S$: C, 49.77; H, 2.78; N, 6.45. Found: C, 49.92; H, 2.97; N, 6.52.

EXAMPLE 9

1-(N,N-Dimethylthiocarbamoyl)-4,5-diphenyl-2-(1,1,2,2-tetrafluoroethylthio)imidazole To a solution of 5.0 g (0.014 mole) of 4,5-diphenyl-2-(1,1,2,2-tetrafluoroethylthio)imidazole in 50 ml of THF was added dropwise 15 ml of 1.6 M methyl lithium solution, followed by a solution of 5.5 g (0.045 mole) of dimethylthiocarbamoyl chloride in 25 ml THF. The reaction mixture was heated at reflux several hours, then concentrated by rotary evaporation. The residue was shaken with ether and 1 N hydrochloric acid. The ether layer was washed with 10% sodium bicarbonate solution, then dried and concentrated. The residue (7.8 g) was purified by chromatography on silica gel, eluting with toluene to give 0.8 g of product, mp 133°–133.5° (recrystallized from methyl cyclohexane).

Anal. Calcd. for $C_{20}H_{17}F_4N_3S_2$: C, 54.67; H, 3.87; N, 9.57. Found: C, 54.30; H, 3.84; N 9.38.

EXAMPLE 10

1-(N,N-Diethylcarbamoyl)-4,5-diphenyl-2-(1,1,2,2-tetrafluoroethylthio)imidazole

A mixture of 2.0 g (0.006 mole) of 4,5-diphenyl-2-(1,1,2,2-tetrafluoroethylthio)imidazole and 10.0 g (0.074 mole) of diethylcarbamoyl chloride was heated at reflux for two hours. Excess diethylcarbamoyl chloride was removed under high vacuum. The residue was chromatographed on silica gel, eluting with toluene, to give 1.5 g of product, mp 108°–9° (from methylcyclohexane).

Anal. Calcd. for $C_{22}H_{21}F_4N_3OS$: C, 58.54; H, 4.66; N, 9.31. Found: C, 58.33; H, 4.72; N, 9.27.

EXAMPLE 11

N-Methyl-N-(methylaminocarbonyl)-4,5-diphenyl-2-(1,1,2,2-tetrafluoroethylthio)imidazole-1-carboxamide To a solution of 15.0 g (0.263 mole) of methyl isocyanate and 5.0 g (0.014 mole) of 4,5-diphenyl-2-(1,1,2,2-tetrafluoroethylthio)imidazole in 50 ml of THF was added a catalytic amount of potassium t-butoxide. The reaction solution was stirred at room temperature for several hours, then concentrated by rotary evaporation. The residue was shaken with ether and 1 N hydrochloric acid. The ether layer was washed with 10% sodium bicarbonate solution, then dried and concentrated. The residue was triturated with pet. ether and collected to give 4.8 g of crystals. A sample of 2.5 g was purified chromatography on silica gel, eluting with chloroform to give 1.3 g of crystalline product (from methyl cyclohexane), mp 107°–108.5°.

Anal. Calcd. for $C_{21}H_{18}F_4N_4O_2S$: C, 54.07; H, 3.86; N, 12.01. Found: C, 54.19, 54.09; H, 3.86, 3.91; N, 11.92, 12.01.

EXAMPLE 12

1-Benzyloxycarbonyl-4,5-diphenyl-2-(1,1,2,2-tetrafluoroethylthio)imidazole

To a solution of 5.0 g (0.014 mole) of 4,5-diphenyl-2-(1,1,2,2-tetrafluoroethylthio)imidazole in 50 ml glyme was added 1.7 g (0.015 mole) of potassium t-butoxide. The mixture was cooled and a solution of 5.0 g (0.029 mole) of benzyl chloroformate in 25 ml glyme was added dropwise. The reaction mixture was stirred at room temperature overnight, then poured onto water. The mixture was extracted with ether and the combined ether extracts were washed, then dried and concentrated to give 12.1 g of crystals. The product was purified by chromatography on silica gel, eluting with toluene, to give 2.1 g of colorless crystals (from hexane), mp 110°–111°.

Anal. Calcd. for $C_{25}H_{18}F_4N_2O_2S$: C, 61.73; H, 3.73; N, 5.76. Found: C, 61.85; H, 3.82; N, 5.62.

EXAMPLE 13

4,5-bis(4-Fluorophenyl)-1-(pivaloyloxymethyl)-2-(1,1,2,2-tetrafluoroethylsulfonyl)imidazole To a solution of 5.0 g (0.012 mole) of 4,5-bis(4-fluorophenyl)-2-(1,1,2,2-tetrafluoroethylsulfonyl)imidazole in 50 ml glyme was added 1.7 g (0.015 mole) of potassium t-butoxide, followed by a solution of 4.6 g (0.031 mole) of chloromethyl pivalate in 25 ml of glyme dropwise and a catalytic amount of potassium iodide. The reaction mixture was heated at reflux overnight, then poured onto water. The aqueous mixture was extracted with ether. The combined ether extracts were washed, then dried and concentrated to give 13.4 g of crude oily product. The product was purified by chromatography on silica gel, eluting with toluene, to give 4.1 g of crystals, mp 121°–123.5° (from methyl cyclohexane).

Anal. Calcd. for $C_{23}H_{20}F_6N_2O_4S$: C, 51.69; H, 3.75; N, 5.24. Found: C, 52.10; H, 3.80; N, 5.10.

EXAMPLE 14

1-Benzenesulfonyl-4,5-diphenyl-2-(1,1,2,2-tetrafluoroethylthio)imidazole

To a stirred solution of 7.0 g (0.02 mole) of 4,5-diphenyl-2-(1,1,2,2-tetrafluoroethylthio)imidazole in 50 ml glyme at 0° was added 3.4 g (0.03 mole) of potassium t-butoxide. The mixture was stirred at 0° for five minutes, then a solution of 5.3 g (0.03 mole) of benzenesulfonyl chloride in 50 ml glyme was added dropwise. The mixture was stirred at 0° for one hour, then at room temperature overnight. The mixture was poured onto ice water and the crude solid product was collected and washed with water and hexane to give 12.4 g of tan solid. The product was purified by chromatography on silica gel, eluting with toluene, to give 7.2 g, white crystals, mp 171.5°–172.5° (from methylcyclohexane).

Anal. Calcd. for $C_{23}H_{16}F_4N_2O_2S_2$: C, 56.09, H, 3.27; N, 5.69. Found: C, 56.45; H, 3.32; N, 5.65.

EXAMPLE 15

1-Acetyl-4,5-diphenyl-2-(1,1,2,2-tetrafluoroethylthio)imidazole

A mixture of 1.8 g (0.005 mole) of 4,5-diphenyl-2-(1,1,2,2-tetrafluoroethylthio)imidazole and 25 ml acetic anhydride was heated at reflux seven hours, then cooled and stirred at room temperature for four days. Most of the acetic anhydride and acetic acid were removed at reduced pressure (~0.5 mm). The white solid residue was chromatographed on silica gel, eluting with toluene, to give 0.8 g of white product, mp 143°–4° (from hexane).

Anal. Calcd. for $C_{19}H_{14}F_4N_2OS$: C, 57.86; H, 3.58; N, 7.10. Found: C, 57.80; H, 3.47; N, 7.25.

EXAMPLE 16

4,5-Diphenyl-2-(1,1,2,2-tetrafluoroethylthio)-1-(2-tetrahydrofuranyl)imidazole

To a stirred solution of 1.8 g (0.005 mole) of 4,5-diphenyl-2-(1,1,2,2-tetrafluoroethylthio)imidazole and 5 g (0.05 mole) triethylamine in 20 ml tetrahydrofuran, was added dropwise at room temperature a solution of 2-chlorotetrahydrofuran, which had been prepared by adding 2.4 g (0.018 mole) of sulfuryl chloride to 30 ml tetrahydrofuran and waiting until the exothermic reaction mixture had returned to room temperature. The reaction mixture was stirred at room temperature for four days, then poured into ice water containing excess sodium bicarbonate. The aqueous mixture was extracted with methylene chloride, which was dried and concentrated. The crystalline residue was purified by chromatography on silica gel, eluting with toluene, to give 1.6 g of product, mp 145°-6° (from methylcyclohexane).

Anal. Calcd. for $C_{21}H_{18}F_4N_2OS$: C, 59.71; H, 4.30; N, 6.63. Found: C, 60.05; H, 4.41; N, 6.66.

EXAMPLE 17

1-Benzenesulfonyl-4,5-bis(4-fluorophenyl)-2-(trifluoromethylthio)imidazole a. To a stirred mixture of 10.0 g (0.04 mole) of 4,5-bis(4-fluorophenyl)imidazole and 4.8 g (0.043 mole) of potassium t-butoxide in 150 ml glyme at 0° was added dropwise a solution of 7.6 g (0.043 mole) of benzenesulfonyl chloride in 25 ml glyme. The mixture was stirred at 0° one hour, then at room temperature overnight. The mixture was poured into ice water and the solid was collected and air dried to give 15.2 g, mp 172°-5°. Recrystallization from toluene/methylcyclohexane gave 12.3 g of 1-benzenesulfonyl-4,5-bis(4-fluorophenyl)imidazole as a white solid, mp 181°-2°.

Anal. Calcd. for $C_{21}H_{14}F_2N_2O_2S$: C, 63.63; H, 3.56; N, 7.07 Found: C, 63.47; H, 3.63; N, 6.97.

b. To a stirred suspension of 5.9 g (0.015 mole) of 1-benzenesulfonyl-4,5-bis(4-fluorophenyl)imidazole and 1.9 g (0.016 mole) of tetramethylethylenediamine in 75 ml ether, at −78° under nitrogen, was added dropwise a solution of 10 ml (0.016 mole) of 1.6 M n-butyl lithium solution in 30 ml ether. The mixture was stirred another fifteen minutes at −78°, then a solution of 3.3 g (0.016 mole) of trifluoromethyl disulfide in 25 ml ether was added dropwise. The mixture was stirred at −78° for one hour, then at room temperature for one hour. Cautiously, a few ml of saturated sodium bicarbonate solution was added, then the entire reaction mixture was poured into a separatory funnel containing 200 ml water and 50 ml saturated sodium bicarbonate solution. The aqueous mixture was extracted several times with ether and the combined ether extracts were dried and concentrated to give crude product. This was purified by chromatography on silica gel, eluting with toluene, to give 2.7 g of 1-benzenesulfonyl-4,5-bis(4-fluorophenyl)-2-(trifluoromethylthio)imidazole as white crystals (from methylcyclohexane/hexane), mp 154°-5°.

Anal. Calcd. for $C_{22}H_{13}F_5N_2O_2S_2$: C, 53.22; H, 2.64; N, 5.64. Found: C, 53.79, 53.40; H, 2.93, 2.75; N, 5.67, 5.70.

A small sample was converted by stirring in ethanol saturated with dry ammonia to 4,5-bis(4-fluorophenyl)-2-(trifluoromethylthio)imidazole, identified by comparison with authentic material prepared by a different route.

EXAMPLE 18

4,5-bis(4-Fluorophenyl)-1-isopropyl-2-(1,1,2,2-tetrafluoroethylthio)imidazole a. A mixture of 30 g (0.121 mole) of 4,4'-difluorobenzoin, 14.3 g (0.121 mole) of N-isopropylthiourea and 100 ml DMF was heated at reflux through molecular sieves for five hours. The mixture was cooled to room temperature and the crystalline product was collected, washed with DMF/water, then water, then dried to give 22.7 g of 4,5-bis(4-fluorophenyl)-1-isopropylimidazole-2-thiol as a pale yellow solid, mp 308°-312°.

b. To a mixture of 10 g (0.03 mole) of the above thiol, 1.2 g (0.012 mole) of di-isopropylamine and 100 ml DMF in a pressure vessel was added 6.1 g (0.061 mole) of tetrafluoroethylene. The mixture was shaken and heated at 50° for eight hours, then cooled and vented. The reaction mixture was poured onto ice water. The solid product was collected, washed with water, then dried to give 11.5 g of crude product, mp 94°-103°. Purification by recrystallization from heptane gave 8.5 g of product, mp 105.5°-107°.

Anal. Calcd. for $C_{20}H_{16}F_6N_2S$: C, 55.81; H, 3.75; N, 6.51. Found: C, 55.78; H, 3.80; N, 6.89.

Using the appropriate starting materials and the procedures described in examples 1-18, the compounds in Table I were prepared.

TABLE I

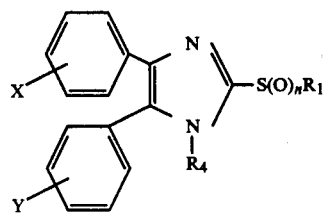

| Example | X | Y | $R_1$ | $R_4$ | n | mp |
|---|---|---|---|---|---|---|
| 19 | 4-F | 4-F | $CF_2CHF_2$ | $CH_3$ | 0 | 100°-101.5° |
| 20 | 4-F | 4-F | $CF_2CHF_2$ | $CH_2CH_3$ | 0 | 74°-75° |
| 21 | 4-F | 4-F | $CF_2CHF_2$ | $CH_2CH_2CH_3$ | 0 | 102.5°-104° |
| 22 | 4-F | 4-F | $CF_2CHF_2$ | $CH_2CH=CH_2$ | 0 | 89.5°-91.5° |
| 23 | 4-F | 4-F | $CF_2CHF_2$ | $CH_2CH_3$ | 2 | 135.5°-137° |
| 24 | 4-F | 4-F | $CF_2CHF_2$ | $CH_2CH_2CH_3$ | 2 | 123°-124.5° |
| 25 | 4-F | 4-F | $CF_2CHF_2$ | $CH_2CH_2CH_2CH_3$ | 2 | 69.5°-71° |
| 26 | 4-F | 4-F | $CF_2CHF_2$ | $CH_2CH=CH_2$ | 2 | 89.5°-91° |
| 27 | 4-F | 4-F | $CF_2CHF_2$ | $CH_2CH_2N(CH_3)_2$ | 2 | 105°-107.5° |
| 28 | 4-F | 4-F | $CF_3$ | $CH_3$ | 0 | 132°-4° |
| 29 | 4-F | 4-F | $CF_3$ | $CH_3$ | 2 | 159°-160° |
| 30 | 4-$CH_3O$ | 4-$CH_3O$ | $CF_3$ | $CH_3$ | 2 | 161°-2° |
| 31 | 4-$CH_3O$ | 4-$CH_3O$ | $CF_2CH_2F$ | $CH_3$ | 2 | 144.5°-145° |

TABLE I-continued

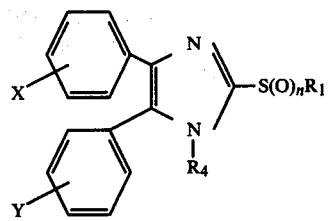

| Example | X | Y | R$_1$ | R$_4$ | n | mp |
|---|---|---|---|---|---|---|
| 32 | H | H | CF$_2$CHF$_2$ | SO$_2$CH$_3$ | 0 | 167°–8° |
| 33 | H | H | CF$_2$CHF$_2$ | CH$_2$OCH$_2$OCH$_3$ | 0 | 63°–63.5° |
| 34 | H | H | CF$_2$CHF$_2$ | C(O)C$_6$H$_5$ | 0 | 125°–7° |

Some additional compounds which could be prepared by the methods described above are noted in Table II.

TABLE II

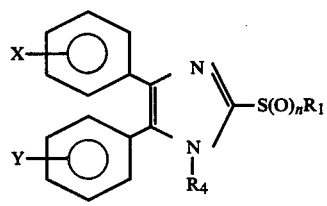

| X | Y | R$_1$ | R$_4$ | n |
|---|---|---|---|---|
| 4-F | 4-F | CF$_3$ | H$_5$C$_2$OCO | 0 |
| 4-F | 4-F | CF$_3$ | φCH$_2$OCH | 2 |
| 4-CH$_3$O | 4-CH$_3$O | CF$_3$CH$_2$ | H$_5$C$_2$OCO | 0 |
| 4-CH$_3$O | 4-CH$_3$O | BrCFHCF$_2$ | 2-tettrahydropyranyl | 0 |
| 4-CH$_3$O | 4-CH$_3$O | BrCFHCF$_2$ | φCH$_2$OCH$_2$ | 2 |
| 4-CH$_3$O | 4-CH$_3$O | H$_2$CFCF$_2$ | H$_5$C$_2$OCO | 0 |
| 4-CH$_3$O | 4-CH$_3$O | H$_2$CFCF$_2$ | φCH$_2$OCH$_2$ | 2 |
| 4-Cl | 4-Cl | HCF$_2$ | H$_3$COCO | 0 |
| 4-n-C$_4$H$_9$ | 4-n-C$_4$H$_9$ | HCF$_2$ | CH$_3$OCH$_2$ | 1 |
| 4-CF$_3$ | 4-CF$_3$ | CH$_3$ | φCH$_2$OCH$_2$ | 0 |
| 3-F | 3-Cl | HCF$_2$CF$_2$ | 2-tetrahydropyranyl | 0 |
| 4-C$_2$H$_5$O | 4-C$_2$H$_5$O | C$_2$H$_5$ | H$_5$C$_2$OCO | 0 |
| C$_2$H$_5$ | C$_2$H$_5$ | HCF$_2$CF$_2$ | φCH$_2$OCH$_2$ | 1 |
| 4-CH$_3$O | 3-F | CH$_2$=CH—CH$_2$ | H$_5$C$_2$OCO | 0 |
| 4-F | 4-F | HCl$_2$CF$_2$ | 2-tetrahydropyranyl | 0 |
| 2-Cl | 2-Cl | HCF$_2$CF$_3$ | φCH$_2$OCH$_2$ | 2 |
| 4-F | 4-F | CF$_3$ | (CH$_3$)$_2$CH | 0 |
| 4-Cl | 4-Cl | CF$_3$ | CH$_3$CH$_2$ | 2 |
| 3-Cl | 3-Cl | HCF$_2$CF$_2$ | CH$_3$CH$_2$CH$_2$ | 1 |
| 4-F | 4-F | n-C$_6$H$_{13}$ | C$_2$H$_5$OCO | 0 |
| 4-F | 4-F | CH$_3$C(O)CH$_2$ | φCH$_2$OCH$_2$ | 0 |
| 4-F | 4-F | CH$_3$SCH$_2$ | CH$_3$OCO | 0 |
| 4-F | 4-F | CF$_3$CF$_2$ | φCH$_2$OCH$_2$ | 2 |
| 4-F | 4-F | CH$_2$=CH | φCH$_2$OCH$_2$ | 2 |
| 4-F | 4-F | CF$_3$ | n-C$_6$H$_{13}$ | 2 |
| 4-F | 4-F | CHF$_2$CF$_2$ | CH$_3$NHCO | 0 |
| 4-F | 4-F | CF$_3$ | (CH$_3$)$_2$NCO | 0 |
| 4-NH$_2$ | 4-NH$_2$ | CHF$_2$CF$_2$ | CH$_3$ | 0 |
| 4-(CH$_3$)$_2$N | 4(CH$_3$)$_2$N | CF$_3$ | C$_2$H$_5$OCO | 0 |
| 4-NO$_2$ | 4-NO$_2$ | CF$_3$ | φOCH$_2$OCH$_2$ | 2 |
| 4-CH$_3$S | 4-CH$_3$S | CHF$_2$CF$_2$ | C$_2$H$_5$OCO | 0 |
| 4-CH$_3$SO$_2$ | 4-CH$_3$SO$_2$ | CF$_3$ | φCH$_2$OCH$_2$ | 2 |
| 3,4-methylenedioxy | 3,4-methylenedioxy | CHF$_2$CF$_2$ | φCH$_2$OCH$_2$ | 0 |
| 3,4-diCl | H | CHF$_2$CF$_2$ | φCH$_2$OCH$_2$ | 2 |
| 4-CH$_3$O | 4-CH$_3$O | CF$_3$ | φCH$_2$OCH$_2$ | 2 |
| 4-CH$_3$O | 4-CH$_3$O | CF$_3$ | C$_2$H$_5$OCO | 0 |
| 4-F | 4-F | CF$_3$ | CH$_3$CH$_2$OCH CH$_3$ | 0 |
| 4-F | 4-F | CHF$_2$CF$_2$ | n-C$_3$H$_7$OCH$_2$ | 0 |
| 4-F | 4-F | CF$_3$ | C$_6$H$_5$CH$_2$C(O)OCH$_2$ | 0 |
| 4-F | 4-F | CHF$_2$CF$_3$ | n-C$_4$H$_9$OC(O) | 0 |
| 4-F | 4-F | CHF$_2$CF$_2$ | n-C$_6$H$_{13}$NHC(O) | 0 |
| 4-F | 4-F | CF$_3$ | n-C$_5$H$_{13}$C(O) | 0 |
| 4-F | 4-F | CHF$_2$CF$_2$ | 4-NO$_2$C$_6$H$_4$C(O) | 0 |
| 4-F | 4-F | CF$_3$ | N-C$_4$H$_9$SO$_2$ | 0 |
| 4-F | 4-F | CHF$_2$CF$_2$ | 4-CH$_3$C$_6$H$_4$SO$_2$ | 0 |

Dosage Forms

The anti-arthritic and analgetic agents of this invention can be administered to treat arthritis and/or pain by any means that produces contact of the active agent with the agent's site of action in the body of a mammal. The compounds of formula I have anti-arthritic properties and in addition some can be used to alleviate pain. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.001 to 40 milligrams per kilogram of body weight. Ordinarily 0.005 to 20, and preferably 0.01 to 4 milligrams per kilogram per day given in divided doses 2 to 4 times a day or in sustained release form is effective to obtain desired results.

Dosage forms (compositions) suitable for internal administration contain from about 0.1 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are critric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 50 milligrams of powdered active ingredient, 110 milligrams of lactose, 32 milligrams of talc, and 8 milligrams magnesium stearate.

Capsules

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is 50 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is sterilized by filtration.

Suspension

An aqueous suspension is prepared for oral administration so that each 5 milliliters contain 10 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Injectable

A parenteral composition suitable for administration by injection is prepared by dissolving 1% by weight of active ingredient in sodium chloride injection U.S.P. XV and adjusting the pH of the solution to between 6 and 7. The solution is sterilized by filtration.

Use

To detect and compare the anti-inflammatory activities of compounds in this series and standard drugs, a test was used based on a standard model of arthritis for which there is good correlation with human efficacy. The model is adjuvant-induced arthritis in rats. Federation Proceedings, Vol. 32, No. 2 1973 "Models Used for the Study and Therapy of Rheumatoid Arthritis'-'—Symposium of the American Society for Pharmacology and Experimental Therapeutics—states "The rat polyarthritis produced by intradermal injection of a suspension of *Mycobacterium tuberculosis* in mineral oil (adjuvant) has been used extensively for the screening of drugs of potential use in rheumatoid arthritis."

Established Adjuvant-Induced Arthritis in Rats

Charles River Lewis male rats (130–150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Nonarthritic controls are injected with mineral oil. The animals are held for two weeks to allow development of arthritis. Paw volumes (uninjected, left hind paw) are measured and the adjuvant injected rats are culled and distributed to treatment groups of 10 of equal disease severity. Nonarthritic controls are distributed to two groups of 10. The rats are given oral doses of compound or PVA-Acacia (Polyvinyl Alcohol 1%, Gum Acacia, U.S.P. 5%, Methylparaben 0.5%) (10 ml/kg) by gavage on that day and on the six following days. One day after the last dose the paw volumes (uninjected, left hind paw) are measured using a Ugo Basile Volume Differential Meter Model 7101.

$$\frac{\text{Arthritic Control} - \text{Treatment Group}}{\text{Arthritic Control} - \text{Non-Arthritic Control}} \times 100 =$$
$$\frac{\text{Mean Paw Volume (ml)} - \text{Mean Paw Volume (ml)}}{\text{Mean Paw Volume (ml)} - \text{Mean Paw Volume (ml)}}$$
% Decrease from Control Mean Paw Volume.

Dose-response regression lines of the percent decrease are plotted on semi-log paper by visual fit and the ED50% decrease from control paw volume is determined by inspection. Data for some of the compounds in this invention are summarized in Table III.

Compounds from this series are many times more potent than aspirin and ibuprofen in the treatment of adjuvant induced arthritis in rats. Many compounds are more potent than phenylbutazone and two compounds are more potent than indomethacin in this test system.

TABLE III

ESTABLISHED ADJUVANT-INDUCED ARTHRITIS IN RATS (A.A.)

| Chemical Example Number | A.A. ED50%* mg/kg | |
|---|---|---|
| 1 | >10 | (34% @ 10 mg/Kg) |
| 2 | 3.7 | |
| 3 | 2.3 | |
| 4 | 1.3 | |
| 5 | 18 | |
| 6 | 0.15 | |
| 7 | 0.65 | |
| 8 | 1.0 | |
| 9 | <15 | (53% @ 15 mg/Kg) |
| 11 | 1.8 | |
| 12 | <25 | (69% @ 25 mg/Kg) |
| 13 | 1.2 | |
| 14 | ~35 | |
| 15 | 0.9 | |
| 16 | 2.7 | |
| 17 | 0.18 | |
| 18 | 10 | |
| 19 | 2.3 | |
| 20 | 3.0 | |
| 21 | 14 | |
| 22 | 1.3 | |
| 23 | 4.8 | |
| 24 | >9 | (33% @ 9 mg/Kg) |
| 25 | 5.0 | |
| 26 | 2.0 | |
| 27 | <7 | (76% @ 7 mg/Kg) |
| 28 | 2.1 | |
| 29 | >3 | (33% @ 3 mg/Kg) |
| 31 | >20 | (36% @ 20 mg/Kg) |
| 32 | ~21 | |
| 34 | 2.3 | |

TABLE III-continued

ESTABLISHED ADJUVANT-INDUCED ARTHRITIS IN RATS (A.A.)

| Chemical Example Number | A.A. ED50%* mg/kg |
|---|---|
| Indomethacin | 0.3 |
| Phenylbutazone | 10 |
| Ibuprofen | 100 |
| Aspirin | 305 |

*Determined as % paw volume reduction from control.

We claim:

1. A compound of the formula

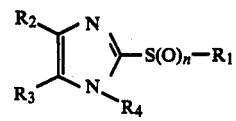

where
n=0, 1, or 2;
R$_1$=C$_1$–C$_6$ alkyl; allyl; vinyl; —CH$_2$COCH$_3$; —CH$_2$-S(O)$_m$CH$_3$, where m=0, 1, or 2; mono- and polyhalo-C$_1$–C$_4$ alkyl;
R$_2$ and R$_3$, the same or different=

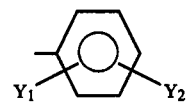

Y$_1$ and Y$_2$, the same or different=hydrogen, C$_1$–C$_4$ alkoxy, C$_1$–C$_4$ alkyl, Cl, F, CF$_3$, NH$_2$, —N(CH$_3$)$_2$, NO$_2$, CH$_3$S—, CH$_3$SO$_2$—, or Y$_1$ and Y$_2$ taken together forming a dioxymethylene bridge;
provided, when R$_1$=C$_1$–C$_4$ alkyl, C$_3$–C$_4$ haloalkyl with halogen substituted at the 3 or 4 position, allyl, or acetonyl, both Y$_1$ and Y$_2$ cannot be H;
R$_4$=C$_1$–C$_6$ alkyl, allyl, CH$_2$CH$_2$N(R$_5$)$_2$,

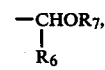

2-tetrahydropyranyl,
2-tetrahydrofuranyl,

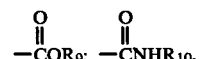

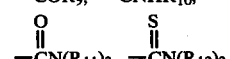

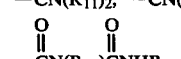

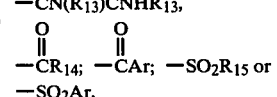

—SO$_2$Ar, where
R$_5$=methyl or ethyl;
R$_6$=H or methyl;
R$_7$=C$_1$–C$_3$ alkyl, benzyl, -CH$_2$CH$_2$OCH$_3$ or —

$R_8$ = $C_1$-$C_4$ alkyl or benzyl;
$R_9$ = $C_1$-$C_4$ alkyl or benzyl;
$R_{10}$ = $C_1$-$C_6$ alkyl;
$R_{11}$ = H, methyl or ethyl;
$R_{12}$ = H, methyl or ethyl;
$R_{13}$ = $C_1$-$C_6$ alkyl;
$R_{14}$ = $C_1$-$C_6$ alkyl;
$R_{15}$ = $C_1$-$C_4$ alkyl;
Ar =

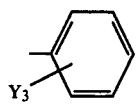

where
$Y_3$ = H, F, Cl, Br, $C_1$-$C_4$ alkyl, $C_1$-$C_4$ alkoxy or nitro;
provided when

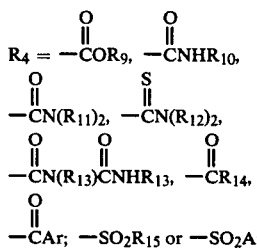

then n must be 0.

2. A compound of claim 1 where $R_1$ = —$CF_2CF_2H$.
3. A compound of claim 1 where $R_1$ = —$CF_3$.
4. A compound of claim 1 where $R_2$ and $R_3$ independently,

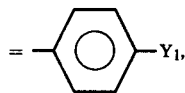

where $Y_1$ = H, Cl, or F.

5. A compound of claim 1 where $R_4$ = alkoxycarbonyl, alkoxymethyl, benzyloxymethyl or pivaloyloxymethyl.
6. A compound of claim 1 where n = 1 or 2.
7. A compound of claim 1 where
$R_1$ = —$CF_2CF_2H$;
$R_2$ and $R_3$, independently,

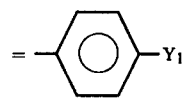

where $Y_1$ = H, Cl, or F; and
$R_4$ = alkoxycarbonyl, alkoxymethyl, benzyloxymethyl or pivaloyloxymethyl.
8. A compound of claim 1 where
$R_1$ = $CF_3$;
$R_2$ and $R_3$, independently,

where
$Y_1$ = H, Cl, or F; and
$R_4$ = alkoxycarbonyl, alkoxymethyl, benzyloxymethyl or pivaloyloxymethyl.
9. The compound of claim 1: 1-benzyloxymethyl-4,5-diphenyl-2-(1,1,2,2-tetrafluoroethylthio)imidazole.
10. The compound of claim 1: 4,5-diphenyl-1-ethoxycarbonyl-2-(1,1,2,2-tetrafluoroethylthio)imidazole.
11. The compound of claim 1: 1-benzyloxymethyl-4,5-diphenyl-2-(1,1,2,2-tetrafluoroethylsulfonyl)imidazole.
12. The compound of claim 1: 4,5-diphenyl-1-(2-tetrahydropyranyl)-2-trifluoromethylthioimidazole.
13. The compound of claim 1: 1-ethoxycarbonyl-4,5-bis(4-fluorophenyl)-2-(1,1,2,2-tetrafluoroethylthio)imidazole.
14. The compound of claim 1: 1-ethoxycarbonyl-4(or 5)-(4-fluorophenyl)-5(or 4)-phenyl-2-(1,1,2,2-tetrafluoroethylthio)imidazole.
15. The compound of claim 1: 4,5-bis(4-fluorophenyl)-1-(pivaloyloxymethyl)-2-(1,1,2,2-tetrafluoroethylsulfonyl)imidazole.
16. A pharmaceutical composition comprising a suitable pharmaceutical carrier and an effective antiarthritic amount of a compound of claim 1.
17. A pharmaceutical composition comprising a suitable pharmaceutical carrier and an effective antiarthritic amount of a compound of claim 2.
18. A pharmaceutical composition comprising a suitable pharmaceutical carrier and an effective antiarthritic amount of a compound of claim 3.
19. A pharmaceutical composition comprising a suitable pharmaceutical carrier and an effective antiarthritic amount of a compound of claim 4.
20. A pharmaceutical composition comprising a suitable pharmaceutical carrier and an effective antiarthritic amount of a compound of claim 5.
21. A pharmaceutical composition comprising a suitable pharmaceutical carrier and an effective antiarthritic amount of a compound of claim 6.
22. A pharmaceutical composition comprising a suitable pharmaceutical carrier and an effective antiarthritic amount of a compound of claim 7.
23. A pharmaceutical composition comprising a suitable pharmaceutical carrier and an effective antiarthritic amount of a compound of claim 8.
24. A pharmaceutical composition comprising a suitable pharmaceutical carrier and an effective antiarthritic amount of the compound of claim 9.
25. A pharmaceutical composition comprising a suitable pharmaceutical carrier and an effective antiarthritic amount of the compound of claim 10.
26. A pharmaceutical composition comprising a suitable pharmaceutical carrier and an effective antiarthritic amount of the compound of claim 11.
27. A pharmaceutical composition comprising a suitable pharmaceutical carrier and an effective antiarthritic amount of the compound of claim 12.
28. A pharmaceutical composition comprising a suitable pharmaceutical carrier and an effective antiarthritic amount of the compound of claim 13.

29. A pharmaceutical composition comprising a suitable pharmaceutical carrier and an effective antiarthritic amount of the compound of claim 14.

30. A pharmaceutical composition comprising a suitable pharmaceutical carrier and an effective antiarthritic amount of the compound of claim 15.

31. A method of treating arthritis in a mammal in need of such treatment which comprises administering to the mammal an effective antiarthritic amount of a compound of claim 1.

32. A method of treating arthritis in a mammal in need of such treatment which comprises administering to the mammal an effective antiarthritic amount of a compound of claim 2.

33. A method of treating arthritis in a mammal in need of such treatment which comprises administering to the mammal an effective antiarthritic amount of a compound of claim 3.

34. A method of treating arthritis in a mammal in need of such treatment which comprises administering to the mammal an effective antiarthritic amount of a compound of claim 4.

35. A method of treating arthritis in a mammal in need of such treatment which comprises administering to the mammal an effective antiarthritic amount of a compound of claim 5.

36. A method of treating arthritis in a mammal in need of such treatment which comprises administering to the mammal an effective antiarthritic amount of a compound of claim 6.

37. A method of treating arthritis in a mammal in need of such treatment which comprises administering to the mammal an effective antiarthritic amount of a compound of claim 7.

38. A method of treating arthritis in a mammal in need of such treatment which comprises administering to the mammal an effective antiarthritic amount of a compound of claim 8.

39. A method of treating arthritis in a mammal in need of such treatment which comprises administering to the mammal an effective antiarthritic amount of the compound of claim 9.

40. A method of treating arthritis in a mammal in need of such treatment which comprises administering to the mammal an effective antiarthritic amount of the compound of claim 10.

41. A method of treating arthritis in a mammal in need of such treatment which comprises administering to the mammal an effective antiarthritic amount of the compound of claim 11.

42. A method of treating arthritis in a mammal in need of such treatment which comprises administering to the mammal an effective antiarthritic amount of the compound of claim 12.

43. A method of treating arthritis in a mammal in need of such treatment which comprises administering to the mammal an effective antiarthritic amount of the compound of claim 13.

44. A method of treating arthritis in a mammal in need of such treatment which comprises administering to the mammal an effective antiarthritic amount of the compound of claim 14.

45. A method of treating arthritis in a mammal in need of such treatment which comprises administering to the mammal an effective antiarthritic amount of the compound of claim 15.

46. A compound of claim 1 wherein at least one of $R_2$ and $R_3 =$

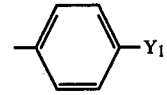

where $Y_1 = C_1-C_4$ alkoxy.

47. A compound of claim 1 wherein $R_4 = -CH_2OCH_2$

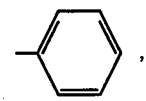

2-tetrahydropyranyl, 2-tetrahydrofuranyl or $-SO_2Ar$.

48. A pharmaceutical composition comprising a suitable pharmaceutical carrier and an effective analgesic amount of a compound of claim 46.

49. A method of treating pain in a mammal in need of such treatment which comprises administering to the mammal an effective analgesic amount of a compound of claim 46.

50. A compound of claim 1 where
n = 0, 1, or 2;
$R_1 = C_1-C_4$ alkyl; allyl; vinyl; $-CH_2COCH_3$; $-CH_2-S(O)_mCH_3$, where m = 0, 1, or 2; mono- and polyhalo- $C_1-C_4$ alkyl;
$R_2$ and $R_3$, the same or different =

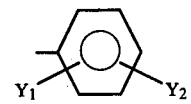

$Y_1$ and $Y_2$, the same or different = hydrogen, $C_1-C_4$ alkoxy, $C_1-C_4$ alkyl, Cl, F, $CF_3$, $NH_2$, $-N(CH_3)_2$, $NO_2$, $CH_3S-$, $CH_3SO_2-$, or $Y_1$ and $Y_2$ taken together forming a dioxymethylene bridge;
$R_4 = C_1-C_3$ alkyl, methoxymethyl, benzyloxymethyl, methoxycarbonyl, ethoxycarbonyl, and 2-tetrahydropyranyl;
provided, when $R_1 = C_1-C_4$ alkyl, $C_3-C_4$ haloalkyl with halogen substituted at the 3 or 4 position, allyl, or acetonyl, both $Y_1$ and $Y_2$ cannot be H.

* * * * *